United States Patent [19]

Rosenthal

[11] Patent Number: 5,618,274
[45] Date of Patent: Apr. 8, 1997

[54] METHOD AND DEVICE FOR DEEP PRESSURIZED TOPICAL, FORNIX APPLIED "NERVE BLOCK" ANESTHESIA

[76] Inventor: Kenneth J. Rosenthal, 4 White Pine La., Kings Point, N.Y. 11023-1704

[21] Appl. No.: 224,832

[22] Filed: Apr. 8, 1994

[51] Int. Cl.⁶ .................................................. A61M 35/00
[52] U.S. Cl. ........................ 604/290; 604/294; 424/427
[58] Field of Search ........................ 604/289, 294–302, 604/30, 35, 50, 290; 128/645, 648; 424/427

[56] References Cited

U.S. PATENT DOCUMENTS

| | | | |
|---|---|---|---|
| 2,527,947 | 10/1950 | Loos | 604/294 |
| 3,630,200 | 12/1971 | Higuchi | 424/427 |
| 3,995,635 | 12/1976 | Higuchi et al. | 424/427 |
| 4,005,191 | 1/1977 | Clark | 424/154 |
| 4,014,335 | 3/1977 | Arnold | 424/427 |
| 4,175,562 | 11/1979 | Honan . | |
| 4,193,401 | 3/1980 | Marinello | 604/294 |
| 5,137,728 | 8/1992 | Bawa | 424/427 |
| 5,147,647 | 9/1992 | Darougar | 424/427 |
| 5,395,618 | 3/1995 | Darougar et al. | 424/427 |

Primary Examiner—John G. Weiss
Assistant Examiner—Mark O. Polutta
Attorney, Agent, or Firm—Gottlieb, Rackman & Reisman, P.C.

[57] ABSTRACT

There is provided a method for applying anesthetic to the eye organ during anterior segment or other ophthalmological surgeries. The method comprises the steps of placing a moisture absorbent member that is substantially soaked in an anesthetic in at least one of the superior fornix and inferior fornix of the eye organ, and thereafter applying pressure of a desired quantity to the absorbent member in order to promote the transport of the anesthetic from the moisture absorbent member into the deeper ocular and adnexal tissues, and ultimately to the nerves located therein.

19 Claims, 3 Drawing Sheets

U.S. Patent  Apr. 8, 1997  Sheet 1 of 3  5,618,274
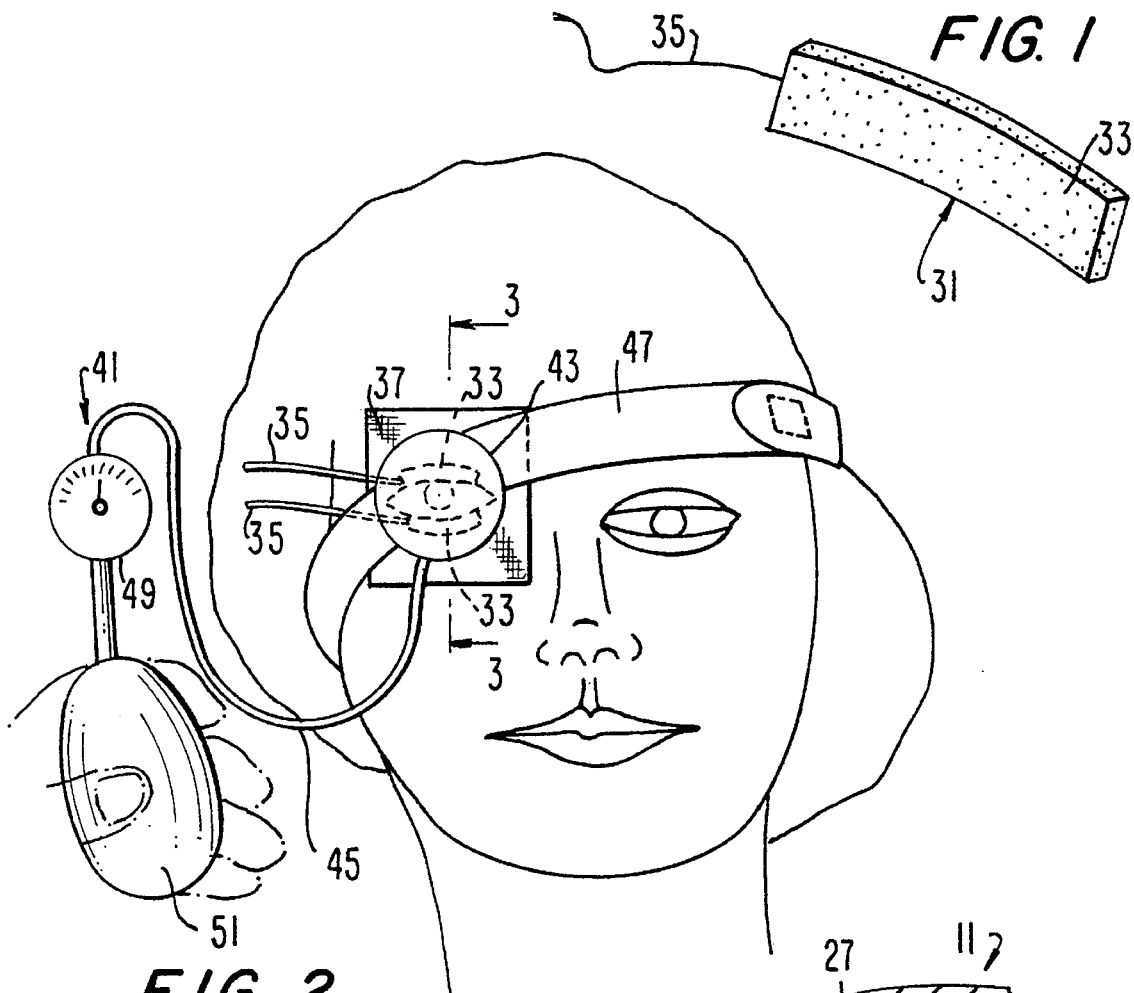
FIG. 1
FIG. 2
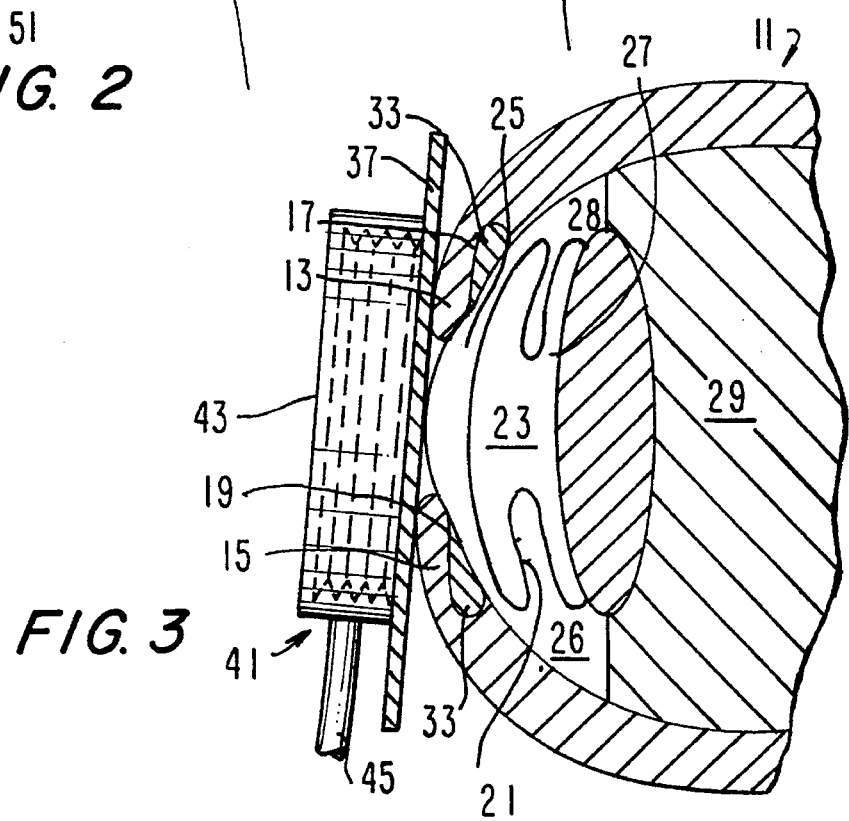
FIG. 3

METHOD AND DEVICE FOR DEEP PRESSURIZED TOPICAL, FORNIX APPLIED "NERVE BLOCK" ANESTHESIA

BACKGROUND OF THE INVENTION

This invention relates to a method for applying a "nerve block" anesthetic to the eye organ prior to or during ophthalmological surgery, and more particularly, to a method and device that is suitable for deep topical fornix "nerve block" anesthesia.

In 1884, Viennese ophthalmogists developed a technique for cataract eye surgery that used a topical cocaine anesthetic. The technique comprised the application of cocaine eye drops onto the ocular surface. The method was advantageous since it avoided the use of a general anesthetic, which carried greater risks to the patient.

During the first World War, Van Lint and O'Brien produced motor akinesia of the facial nerve. Shortly thereafter, in 1928, Professor Elshnig proposed the technique of retrobulbar injection, which comprises injection of anesthetic into the retrobulbar space of the eye organ using a hypodermic needle.

Since that time, there has been continuing debate about what type of anesthetic technique is appropriate in ocular anterior segment surgery. The retrobulbar injection anesthesia technique produces profound anesthesia (loss of sensation) as well as akinesia (loss of motion) and increased stability of the eye organ globe during surgery. It also facilitates free manipulation of the external as well as internal anterior eye segment structures. However, retrobulbar injection does not anesthetize much of the conjunctival surface.

Traditional topical anesthesia, on the other hand, allows for more rapid onset of the anesthesia to take effect and has less risk of damage to the eye organ. However, in the ophthalmological art, it is generally known that a topical anesthetic produces some degree of patient pain or sensation when making incisions in the sclera and when manipulating the iris and ciliary body.

Recently, Dr. Spencer Thornton developed a technique of "deep topical anesthesia" for radial keratotomy surgery. This technique comprised carefully instilling proparacaine (ophthaine) in the superior and inferior conjunctival fornices of the eye organ. The technique provides primarily for patient comfort; no anesthetic is placed directly on the cornea of the eye, which is more sensitive than the conjunctiva. Instead, the anesthetic is washed onto the cornea as the patient blinks.

While the technique of deep topical anesthesia of Dr. Thornton was advantageous in some respects to conventional topical application, or the technique of retrobulbar injection, it is less than satisfactory since it does not provide profound anesthesia. Specifically, deep topical anesthesia does not promote access of the anesthetic to posterior and deep orbital compartments.

Accordingly, it would be desirable to develop a method or technique for applying an anesthetic to the eye organ prior to or during anterior eye segment surgery, such as cataract surgery or radial keratotomy, which overcomes the disadvantages that are found in prior art techniques.

SUMMARY OF THE INVENTION

Generally speaking, in accordance with the invention, there is provided a method for applying anesthetic to the eye organ during anterior segment or other ophthalmological surgeries. The method comprises the steps of placing a moisture absorbent member that is substantially soaked in an anesthetic in at least one of the superior fornix and inferior fornix of the eye organ, and thereafter applying pressure of a desired quantity to the absorbent member in order to promote the transport of the anesthetic from the moisture absorbent member into the deeper ocular and adnexal tissues, and ultimately to the nerves located therein.

In one embodiment, a cottonoid or other soft absorbent member, which has been soaked in an anesthetic, is placed as deeply posterior as possible into the superior fornix. A similar member is placed as deeply posterior as possible into the inferior fornix of the eye organ. Then, an inflatable balloon patch, such as Honan's balloon, is placed over the closed eyelid and inflated. This causes the rapid release and dissemination of the anesthetic that is retained in the cottonoid, which is transported and absorbed by the nerve trunks subserving the conjunctiva. Moreover, the anesthetic is transported posteriorly into the parabulbar area, anesthetizing the posterior ciliary nerves, the anterior conjunctiva and limbus, as well as the iris and ciliary body.

In an alternative application of the technique, a specially constructed device comprising a pre-formed cellulose sponge and a flexible, inflatable bladder disposed therein is used. The sponge is first soaked in the desired anesthetic, after which it is placed in the superior fornix and/or inferior fornix of the eye organ, as described above. Then, the bladder that is disposed within the sponge is inflated by using an external pump in order to press the sponge against the conjunctiva, promoting dissemination of the anesthetic across the conjunctival membrane to the surrounding portions of the eye.

The method or technique of the invention incorporates the safety, comfort, ease of administration, as well as rapid onset of conventional topical ophthalmological anesthetic applications. Moreover, the method also exhibits the profunditity and anatomical distribution advantages of retrobulbar or parabulbar anesthetic injections. In this regard, application of an ophthalmological anesthetic in accordance with the invention anesthetizes the majority of the anterior segment of the eye, while sparing anesthesia of the optic nerve. This facilitates rapid return of vision after surgery.

The scope of anesthetic application in a manner in accordance with the invention is actually greater than that achieved by retrobulbar injection if one considers the areas that are surgically manipulated in anterior segment surgery.

Accordingly, it is an object of the invention to provide an improved method for applying an anesthetic to the eye organ for anterior segment ophthalmological surgery, including but not limited to cataract surgery.

It is still another object of the invention to provide an improved method for applying a surgical anesthetic to the eye organ which is safe and comfortable for the surgical patient.

Yet another object of the invention is to provide an improved method for applying a surgical anesthetic to the eye organ which has a more rapid onset rate as well as a faster decay rate as compared to retrobulbar injection.

Still a further object of the invention is to provide an improved method for applying a surgical anesthetic to the eye organ which is easily and quickly applied in advance of the surgical procedure.

Another object of the invention is to provide an improved method for applying a surgical anesthetic to the eye organ which has improved profunditity of anesthesia and anatomical distribution.

Still another object of the invention is to provide a device for applying a surgical anesthetic to an eye organ which increases the number of anatomic areas of the eye organ which are anesthetized, both anteriorly and posteriorly.

Still other objects and advantages of the invention will in part be obvious and will in part be apparent from the specification.

The invention accordingly comprises the several steps and relation of one or more of such steps with respect to each of the others, and the devices embodying the features or construction, combination of elements and arrangement of parts which are adapted to effect these steps, all as exemplified in the following detailed disclosure, and the scope of the invention will be indicated in the claims.

BRIEF DESCRIPTION OF THE DRAWINGS

For a fuller understanding of the invention, reference is made to the following description, taken in connection with the accompanying drawings, in which:

FIG. 1 is a perspective view of an absorbent member, such as a cottonoid, that has been soaked in an anesthetic and that is used in the method of the subject invention;

FIG. 2 is a front-elevational view illustrating the use of an external balloon assembly for applying pressure along a patient's eye in order to cause rapid release and enhanced transport along the parabulbar area of anesthetic soaked in one or more absorbent members that have been placed in the superior fornix and/or inferior fornix of the patient's eye organ;

FIG. 3 is a cross-sectional view taken along line 3—3 of FIG. 2;

DETAILED DESCRIPTION OF THE PREFERRED EMBODIMENTS

Figure 4:
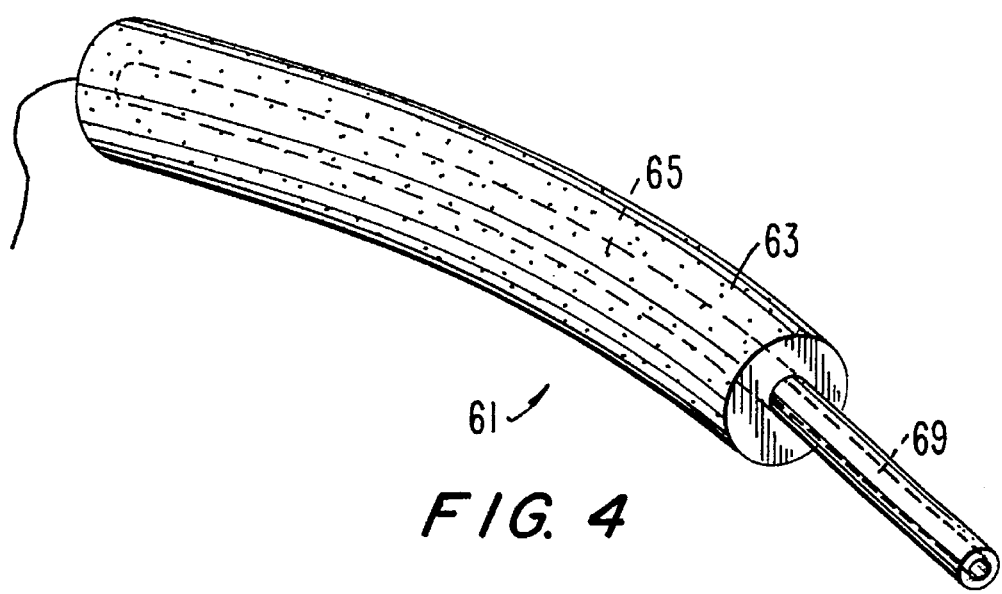
FIG. 4 is a perspective view of a cellulose sponge with a flexible, inflatable bladder made in accordance with the invention.

Referring first to FIGS. 1–3, there is illustrated a first embodiment for employing the technique for applying a surgical anesthetic to a patient's eye organ in accordance with the invention. As shown in FIG. 3, eye organ 11 includes cornea 25, iris 21, pupil 23, ciliary body 26, anterior chamber 27, lens 28 and vitreous 29. Eye organ 11 further includes an upper eyelid 13 and a lower eyelid 15. Eyelid 13 defines a superior cul-de-sac or fornix 17, while lower eyelid 15 defines an inferior cul-de-sac or fornix 19.

Referring specifically to FIG. 1, an elongated rectangular configured cottonoid 31 or other absorbent member is shown, which is placed into either the superior fornix or inferior fornix of the eye organ when carrying out the inventive technique, as described below. Cottonoid 31 is made of a soft puffed cotton material which defines a cotton strip 33. Cottonoid 31 includes a retrievable string 35 extending therefrom for retrieving cottonoid 31 from under the patient's eyelid after anesthetic application has been completed.

Turning now to FIGS. 2 and 3, a balloon inflating assembly, generally indicated at 41, such as a Honan's balloon, is described, which is used in conjunction with cottonoid 31 in order to administer anesthetic to the patient's eye. Balloon assembly 41 includes an inflatable balloon member or patch 43, the outside of which is made of a flexible and expandable rubber-like material. Balloon patch 43 may be mounted over the patient's closed eyelid by means of a headband 47, as best shown in FIG. 2. A gauze pad 37 may be applied between the eyelid of the patient and balloon patch 43, in order to maintain sanitary conditions.

Balloon assembly 41 further includes a squeezable bulb 51 and a length of tubing 45 that is connected at one end to bulb 51 and at the other end to balloon patch 43. Thus, when bulb 51 is repeatedly squeezed, air flows through tubing 45 and into balloon patch 43 such that patch 43 is selectively inflated. A pressure gauge 49 is mounted along tubing 45, as is well known in the art, in order to measure the pressure of inflation of patch 43.

In use, cotton strip 33 of cottonoid 31 is substantially soaked in the desired anesthetic after which it is placed in one of either the superior fornix or inferior fornix of the patient's eye organ (see FIG. 3). Then, balloon patch 43 is inflated by operating balloon assembly 41, as described above, until the desired balloon pressure is reached. Then, the cottonoid is left in place underneath the patient's eyelid for a desired period of time to enable a substantial quantity of the anesthetic to be delivered to the eye organ. Once anesthetic delivery is completed, the cottonoid may be removed from underneath the eyelid utilizing retrievable string 35. The physician is then able to begin the ophthalmological surgical procedure.

Figure 5:
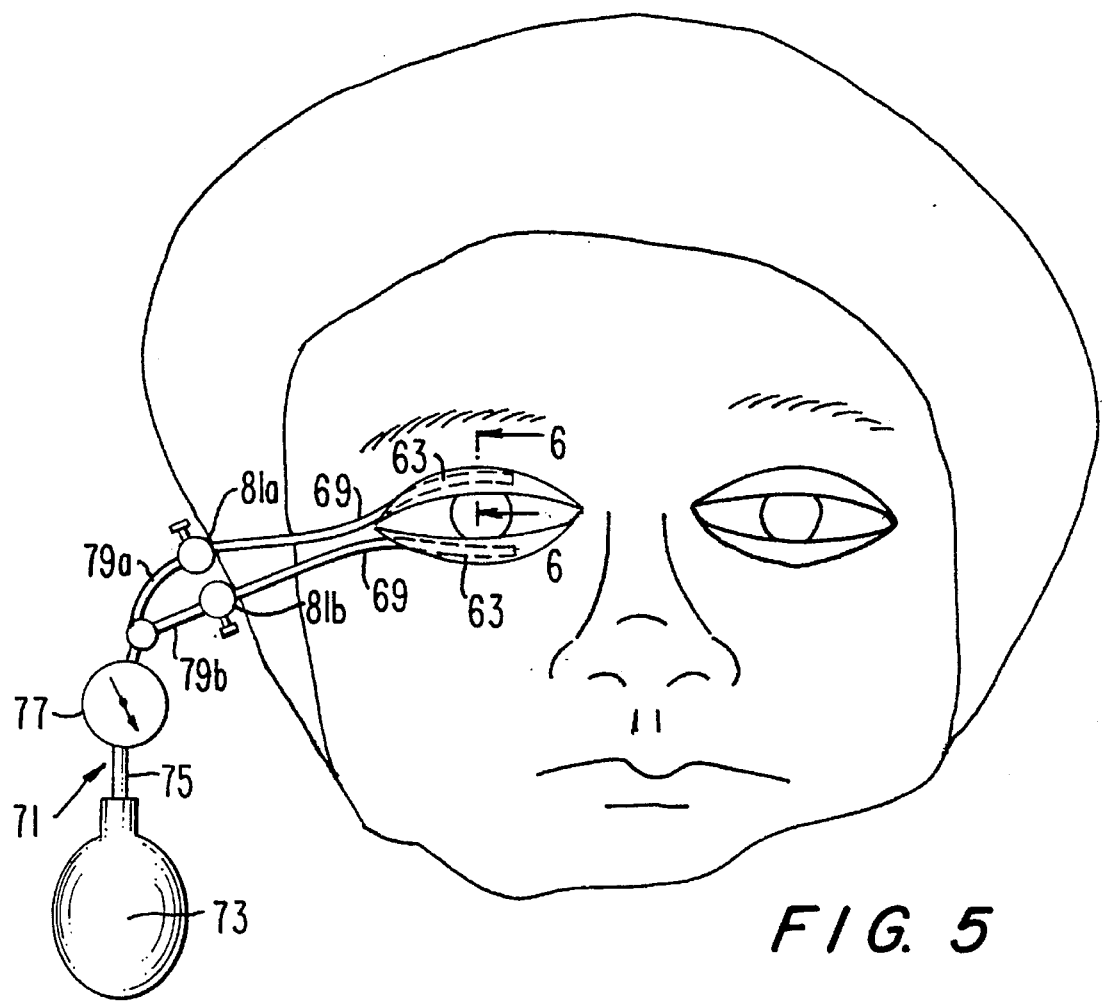
FIG. 5 is a front elevational view illustrating the use of an inflation assembly in connection with the cellulose sponge of FIG. 4.

Turning now to FIGS. 4–7, a second embodiment or system for applying a surgical anesthetic to a patient's eye organ is described. Referring first to FIG. 4, there is provided a novel inflatable sponge assembly generally indicated at 61, which is capable of being inserted under one of the patient's eyelids (in the superior and/or inferior fornix of the conjunctiva) in order to deliver anesthetic to the patient's eye organ. Assembly 61 comprises a substantially cylindrically flexible sponge 63 that is preferably made of a cellulose or other absorbent material and a flexible, inflatable bladder 65 longitudinally disposed therein. Bladder 65 is made of a rubber-like material and is connected to a tubing 69 extending from sponge assembly 61, as best shown in FIG. 5. Tubing 69, during use of assembly 61 in anesthetic delivery to the eye organ, is connected to an air source so that bladder 65 may be selectively inflated and deflated as desired. A retrievable string 67 may be provided on the other end of sponge assembly 61 and may be used for retrieving assembly 61 after use.

Turning now to FIG. 5, there is described one type of inflation assembly, generally indicated at 71, that is selectively connectable to a pair of inflatable sponges 63 disposed underneath the eyelids of the patient, as described above. Inflation assembly 71 comprises a squeezable bulb 73, connecting tubing 75 and a pressure gauge 77 mounted on tubing 75, as is well known in the art. Tubing 75 branches into tubing segments 79a and 79b, each of which is fitted with a valve member 81a and 81b, respectively. Tubing 79a leads into tubing 69 extending from sponge 63 disposed underneath the patient's upper eyelid, while tubing 79b leads into tubing 69 which extends from sponge 63 located behind the patient's lower eyelid valves 81a and 81b are used to selectively open and close the air pathway in each of tubings 79a and 79b.

Figure 6:
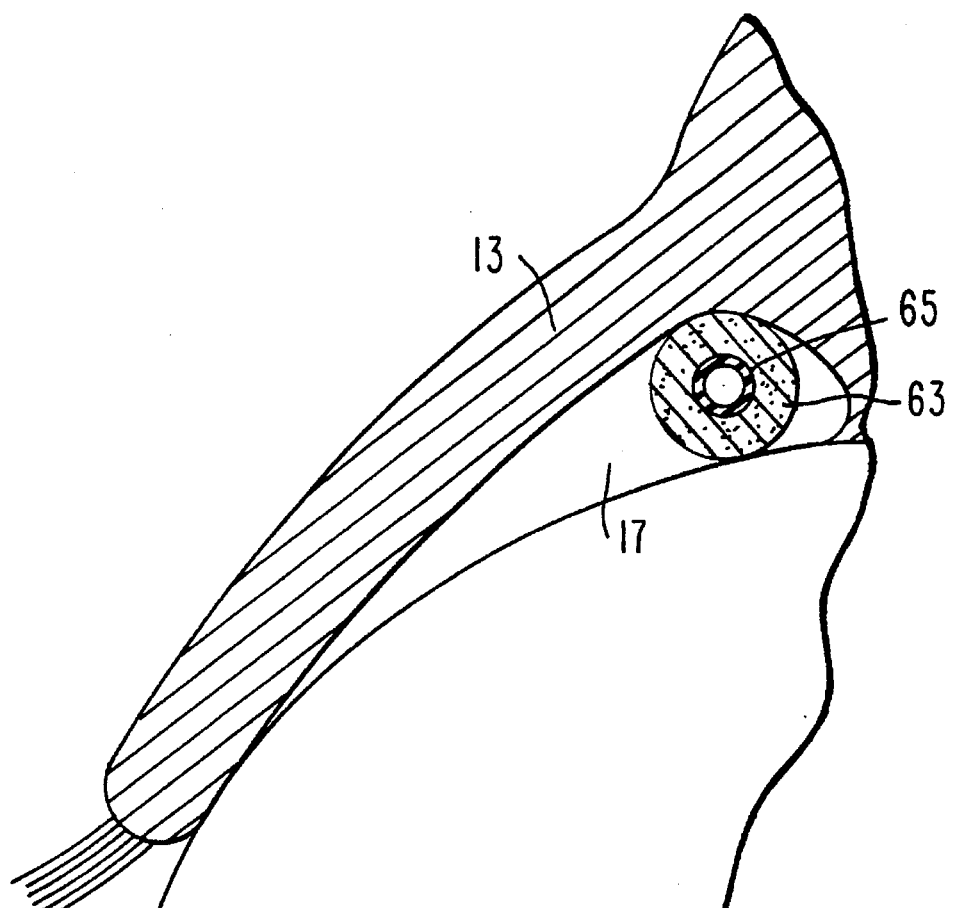
FIG. 6 is a side view in partial cross-section of the eye organ showing placement of the sponge of FIG. 4 before its internal bladder has been inflated.
Figure 7:
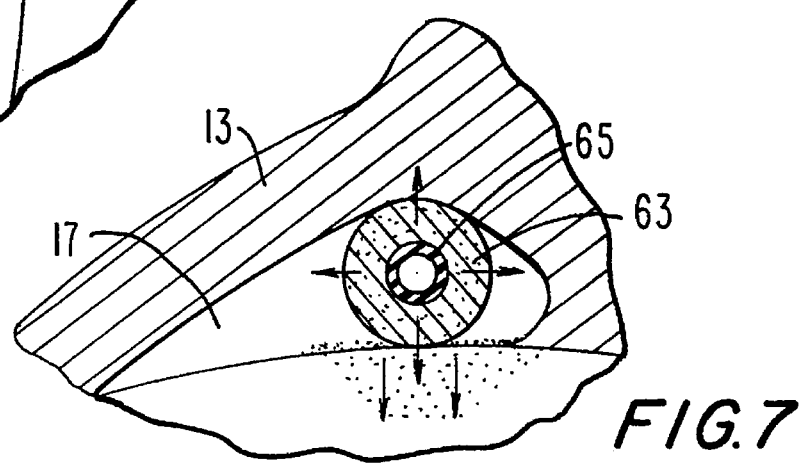
FIG. 7 is a cross-sectional view similar to FIG. 6 in which the internal bladder of the FIG. 4 sponge has been inflated.

Use of this alternative system, as shown in FIGS. 4–7, is now described. Sponge 63 of inflatable sponge assembly 61 is first inserted or placed in superior fornix 17 located behind upper eyelid 13 of the patient, as shown in FIG. 6. Sponge 63 has been pre-soaked in the desired anesthetic agent. Then, inflation assembly 71 is operated in order to inflate balloon 65 disposed within sponge 63 to a desired pressure, as best shown in FIG. 7. Once desired inflation is achieved, valve 81a is closed so that air does not escape from inflatable balloon 65—the inflated sponge is then allowed to sit in place behind the patient's eyelid for a desired period of time in order to allow delivery and transport of anesthetic to the eye organ, as shown by the arrows in FIG. 7. When anesthetic delivery is completed, valve 81a is opened, permitting air in inflatable balloon 65 of sponge assembly 61 to exit, thereby deflating sponge assembly 61. Assembly 61 may then be removed from underneath the patient's upper eyelid by means of retrieval string 67.

Since inflation assembly 71, as shown in FIG. 5, can operate a pair of inflatable sponge assemblies, one disposed underneath the upper lid and the second disposed underneath the lower lid, the physician or other medical professional operating assembly 71 simply opens and closes the valves 81a and 81b as required in order to enable proper inflation of each of sponge assemblies 61.

In order to better illustrate the inventive technique and system, a clinical study was conducted on 81 human eye organs of ophthalmological patients. These patients were first given 1–2 mg. of Versed IV in order to produce sedation. The Versed IV was titrated by an anesthesiologist so that the patient would remain comfortable, but nevertheless sufficiently alert so that he or she could communicate with the eye surgeon. Additional sedation was given to a few of the patients in order to ease their pre-operative anxieties.

Then, several drops of tetracaine or proparacaine were dispensed into the superior and inferior fornices of each of the patients. After a few moments, a cottonoid of a 0.5 inch by 1.5 inches size, which had been soaked in lidocaine 4% solution, was placed into each of the fornices. Then, a balloon patch assembly, such as a Honan's balloon, as is well known in the art, was inflated to 30–35 mm HG and positioned over the patient's eye (see FIG. 2) for about 8 to 10 minutes while the eye surgeon scrubbed for surgery. Thereafter, each of the sponges was removed from underneath the patient's eyelids, and the effect of the topical fornix anesthetic was tested by grasping the limbus of the eye with a surgical forceps.

77 of the procedures were performed with a 5 or 6 mm scleral tunnel, standard continuous tear capsulorhexis and phacoemulsification within the capsular bag usually with a divide and conquer, flit and chip or phacochop technique, in conjunction with Healon or Healon GV as viscoelastic. A single piece PMMA IOL was placed into the capsular bag.

The other four cases were performed using clear cornea with foldable IOL. This technique was used in those patients who were on anticoagulants which were not discontinued for surgery.

Earlier cases were given Miochol at the conclusion of the procedure, but this practice was discontinued as smaller capsulorhexes were used and the lenses were found to be stable in the bag.

After the procedure, each of the patients was sent home with directions to take certain post-operative medications (Inflammase Forte, Ciloxan (or Tobrex) and Betopic-S).

Each patient's visual acuity was tested within 15 minutes of completion of surgery and the following day an assessment was made of post-operative acuity, cell and flare and corneal appearance. Moreover, each patient was questioned about his or her experience at having surgery, i.e., was there some presence of pain or other sensation? As a note, six of the patients previously had cataract surgery on the other eye using a retrobulbar anesthetic and were asked to compare the present procedure to the earlier procedure.

RESULTS

Visual acuity immediately following surgery:
  30% 20/40 or better
  46% 20/50-20/100
  15% 20/100
  9% not tested
Visual acuity on post op day one:
  58% 20/40 or better
  38% 20/50-20/100
  4% 20/100 or worse
Cell and Flare on post op day one:
  73% trace to 1+
  15% 1–2+
  2% 3+–4+

9% of the patients were noted to have mild SPK (superficial punctate keratitis) on the first post operative day. Only two of these patients, both with pre-existing tear film deficiency, had SPK which persisted.

There were only two patients who noted pain during the procedure: one required retrobulbar injection and one required subconjunctival injection.

Postoperatively, most patients needed only a single dose of gr. X of Tylenol. One patient did receive Toradol.

Significantly, none of the procedures required any additional sedation during the incision of the sclera or manipulation of the iris.

Moreover, for all patients there was no post-operative ptosis.

Of the 6 patients who had had retrobulbar or parabulbar anesthetic during prior surgery on their other eye, when comparing the present procedure to that earlier procedure, none was able to discern any difference in terms of comfort or pain.

The results of the study indicate that the inventive technique is very effective in applying anesthetic to the eye organ. In the patient population, there was the presence of lid hypokinesis and the ability to freely manipulate the iris without pain. Moreover, there were few cases of transient superior rectus paresis.

In the technique of the invention, the preferred anesthetic is lidocaine 4% because of its low ocular toxicity and ready commercial availability. Moreover, lidocaine 4% has a pharmacology, potency and absorption that is similar to cocaine 4%, but without the ocular toxicity of cocaine 4%. Since lidocaine is an amide, it tends to bind to protein and is therefore extremely permeable across the conjunctival membrane and into the retrobulbar space of the eye organ, thereby accounting for its profound anesthetic effect.

Although lidocaine 4% is the preferred anesthetic, other anesthetics may be selected without departing from the spirit and scope of the invention. Such anesthetics include lidocaine 2% cocaine proparacaine, mepivacaine and other amide and ester anesthetics, as is well known in the art.

The amount or quantity of anesthetic that is to be applied to the eye organ in carrying out the anesthetic technique of the invention is between about 1 and 10 milliliters.

The topical fornix anesthetic technique of the invention allows for absorption of the anesthetic in the nerve trunks subserving the conjunctiva, Tenon's capsule and sclera. At the same time, since the anesthetic is transported posteriorly into the parabulbar region, the posterior ciliary nerves, which supply the anterior sclera, anterior conjunctiva and limbus, as well as the iris and ciliary body, are anesthetized at their nerve roots.

In addition, because pressure is applied by either an external balloon patch (i.e., a Honan's balloon) or by means of the inventive sponge with inflatable bladder, the transport across the conjunctiva is substantially enhanced, facilitating absorption of the anesthetic into the parabulbar space and ultimately through Tenon's to the sclera posteriorly.

Accordingly, the inventive technique or method achieves the depth of that previously achieved by an injectable deep anesthetic (retrobulbar injection), but is safer and easier to use, since it is topically applied. Thus, a surgeon, who might otherwise be wary of a topical anesthetic, is afforded the comfort of more profound anesthesia without the risks attendant to an injection system.

Furthermore, use of the inventive technique may obviate the need for further depth of sedation, thereby eliminating a further anesthetic risk.

Moreover, the sponge assembly depicted in FIG. 4 may be prepackaged for sale in either a dry condition, whereby the sponge would first have to be soaked in anesthetic before use, or in an already anesthetically soaked condition.

Depending on how fast-acting the selected anesthetic is, and the type of surgery to be performed, the anesthetically soaked absorbent member can either be removed before the surgical procedure, left in under the patient's eyelid during surgery, or even left under in the eyelid after surgery in order to reduce postoperative patient pain.

In accordance with the invention, pressure is applied along the absorbent member in an amount between about 10 and 50 mm HG. In this pressure range, absorption into the eye tissue is encouraged while at the same time precluding any risk of ocular damage.

In addition, pressure is applied along the absorbent member from between 5 and 30 minutes prior to surgery, depending on surgical conditions, in order to allow for sufficient diffusion of anesthetic into the eye tissues. Alternatively, the anesthetically soaked sponge could be left in place underneath the patient's eyelid during the surgical procedure itself.

Although the inventive technique is shown to be used for applying anesthetic to the eye organ, it may also be used to apply other medications, such as cortico steroids, antibiotics and non-steroid anti-inflammatories.

Although the inventive technique is shown to include the step of applying pressure to the anesthetically soaked absorbent member, the technique may also be performed without any pressure application. This situation relies on the active and passive transport of a high concentration and volume of the anesthetic (that was soaked in the absorbent member) into the adjacent tissues, and the pressure generated by the naturally occurring elasticity of the surrounding tissues.

It will thus be seen that the objects set forth above, among those made apparent from the preceding description, are efficiently attained, and since certain changes may be made in carrying out the above method, and in the devices described above, without departing from the spirit and scope of the invention, it is intended that all matter contained in the above description and shown in the drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed:

1. A system for applying an anesthetic or other medication to an eye organ comprising:

a moisture absorbent member that is substantially soaked in said anesthetic or other medication and is placed posteriorly under a patient's eyelid in at least one of the superior and inferior fornices of said eye organ; and means for applying pressure to the absorbent member when placed in one of the superior and inferior fornices of said eye organ in order to promote transport of anesthetic or other medication from the moisture absorbent member into the tissues of said eye organ, said pressure-applying means comprising a selectively inflatable balloon eye patch configured for selective placement over a closed eyelid of the eye organ.

2. The system of claim 1, wherein the absorbent member is made of cotton.

3. The system of claim 1, wherein the absorbent member is made of cellulose.

4. The system of claim 1, wherein said pressure applying means includes means for selectively inflating said balloon eye patch.

5. The system of claim 4, wherein said inflating means comprises a selectively compressible bulb and a tubing extending from said bulb and leading into a said balloon eye patch.

6. A system for applying an anesthetic or other medication in an eye organ comprising:

a moisture absorbent member that is substantially soaked in said anesthetic or other medication and is placed posteriorly under the patient's eyelid in at least one of the superior and inferior fornices of said eye organ; and means for applying pressure to the absorbent member when placed in one of the superior and inferior fornices of said eye organ in order to promote transport of anesthetic or other medication from the moisture absorbent member into the tissues of said eye organ, wherein said pressure-applying means comprises a selectively inflatable internal bladder disposed within said moisture absorbent member.

7. The system of claim 6, wherein said pressure applying means further includes means for selectively inflating said internal bladder.

8. The system of claim 7, wherein said inflating means comprises a selectively compressible bulb and a tubing extending from said bulb and leading into said internal bladder.

9. A system for applying an anesthetic or other medication in an eye organ comprising:

a moisture absorbent member that is substantially soaked in said anesthetic or other medication and is placed posteriorly under the patient's eyelid in at least one of the superior and inferior fornices of said eye organ; and means for applying pressure to the absorbent member when placed in one of the superior and inferior fornices of said eye organ in order to promote transport of anesthetic or other medication from the moisture absorbent member into the tissues of said eye organ, and means for detecting pressure applied by said pressure-applying means.

10. The system of claim 9, wherein the anesthetic is selected from the group consisting of lidocaine 4%, lidocaine 2%, cocaine proparacaine, mepivacaine and other amide and ester anesthetics.

11. The system of claim 10, wherein the anesthetic is lidocaine 4%.

12. A method for applying an anesthetic or other medication to an eye organ comprising the steps of:

placing posteriorly a moisture absorbent member that is at least partially saturated with said anesthetic or other medication under a patient's eyelid in at least one of the superior and inferior fornices of said eye organ; and applying pressure to the absorbent member in order to substantially enhance transport of the anesthetic or other medication from the moisture absorbent member into the tissues of the eye organ by placing a selectively inflatable balloon eye patch over a closed eyelid of the eye organ and inflating said patch.

13. The method of claim 12, wherein the absorbent member is saturated with anesthetic in an amount between about 1 and 10 mls.

14. The method of claim 12, wherein pressure is applied in an amount between about 10 and 50 mm HG.

15. The method of claim 12, wherein pressure is applied for between about 5 and 30 minutes.

16. A method for applying an anesthetic or other medication to an eye organ comprising the steps of:

placing posteriorly a moisture absorbent member that is at least partially saturated with said anesthetic or other medication under a patient's eyelid in at least one of the superior and inferior cornices of said eye organ; and applying pressure to the absorbent member in order to substantially enhance transport of the anesthetic or other medication from the moisture absorbent member into the tissues of the eye organ by disposing a selectively inflatable bladder internally within said absorbent member and inflating said bladder.

17. The method of claim 16, further including the step of soaking the absorbent member in said anesthetic prior to said placing step.

18. The method of claim 16, wherein the absorbent member is saturated with anesthetic in an amount between about 1 and 10 mls.

19. The method of claim 16, wherein pressure is applied in an amount between about 10 and 50 mmHG.

* * * * *